(12) United States Patent
Hassan et al.

(10) Patent No.: US 9,339,184 B2
(45) Date of Patent: May 17, 2016

(54) CONTACT LENS FOR VITREORETINAL SURGERY

(71) Applicant: Insight Instruments, Inc., Stuart, FL (US)

(72) Inventors: Tarek Shawky Hassan, Ann Arbor, MI (US); K. Peter Luloh, Stuart, FL (US); Michael Annen, Ft. Pierce, FL (US)

(73) Assignee: Insight Instruments, Inc., Stuart, FL (US)

( * ) Notice: Subject to any disclaimer, the term of this patent is extended or adjusted under 35 U.S.C. 154(b) by 0 days.

(21) Appl. No.: 14/248,850

(22) Filed: Apr. 9, 2014

(65) Prior Publication Data

US 2014/0307229 A1    Oct. 16, 2014

Related U.S. Application Data

(60) Provisional application No. 61/810,895, filed on Apr. 11, 2013, provisional application No. 61/888,708, filed on Oct. 9, 2013.

(51) Int. Cl.
| | |
|---|---|
| *A61B 3/00* | (2006.01) |
| *G02C 7/00* | (2006.01) |
| *A61B 3/10* | (2006.01) |
| *A61B 3/125* | (2006.01) |
| *A61F 9/007* | (2006.01) |

(52) U.S. Cl.
CPC .............. *A61B 3/125* (2013.01); *A61F 9/00736* (2013.01)

(58) Field of Classification Search
CPC .......... A61B 3/125; A61B 3/103; A61B 3/14; A61B 3/113; A61B 3/1225; A61B 3/1015; A61B 3/107; G02C 5/00; G02C 7/02; G02C 7/04
USPC ......... 351/219, 200, 205, 206, 210, 221, 246, 351/247, 41, 159.01, 159.02
See application file for complete search history.

(56) References Cited

U.S. PATENT DOCUMENTS

| | | | |
|---|---|---|---|
| 3,962,505 A | 6/1976 | Avery | |
| 5,963,301 A | 10/1999 | Volk | |
| 6,120,147 A | 9/2000 | Vijfvinkel et al. | |
| 6,797,003 B1 | 9/2004 | Blake et al. | |
| 2003/0056281 A1* | 3/2003 | Hasegawa | 2/428 |
| 2012/0089073 A1 | 4/2012 | Cunningham, Jr. | |
| 2012/0099077 A1 | 4/2012 | Abt | |
| 2014/0307229 A1 | 10/2014 | Hassan et al. | |
| 2015/0089727 A1* | 4/2015 | Chiang | 2/440 |

* cited by examiner

*Primary Examiner* — Dawayne A Pinkney
(74) *Attorney, Agent, or Firm* — Beusse Wolter Sanks & Maire, PLLC; James H. Beusse

(57) ABSTRACT

A contact lens assembly has a central lens and a circumscribing flange, the lens having an eye contact surface shaped generally to a radius of curvature of a cornea of an eye. The flange comprises a sterile sponge-like liquid absorbent flexible material having a central aperture for fitting snugly about an outer circumference of the lens and extending radially outward therefrom. The flange may include an inner attachment ring for attachment to the outer circumference of the central contact lens.

14 Claims, 6 Drawing Sheets

CONTACT LENS FOR VITREORETINAL SURGERY

CROSS-REFERENCE TO RELATED APPLICATION

This application claims the benefit of U.S. Provisional Application No. 61/810,395, filed Apr. 10, 2013 and U.S. Provisional Application No. 61/888,808, filed Oct. 9, 2013, and incorporated herein by reference in its entirety.

BACKGROUND OF THE INVENTION

The present invention relates to a contact lens for use in vitreoretinal surgery, sometimes referred to as vitrectomy lens, and more particularly, to method and structure for maintaining contact lens position on an eye during surgery.

Vitreoretinal surgery is generally performed by a surgeon using an ophthalmic microscope to peer into the eye. Because of the optics of the eye itself, it is difficult to focus the microscope onto parts of the eye that are toward the rear portion. For this reason, surgeons typical employ a separate lens that can be placed directly on the eyeball and allow focusing to be extended to the retina and other areas in the back of the eyeball. However, the lens placed on the eyeball floats on a thin layer of fluid and tends to slide about the surface of the eye. One method that has been used to overcome this sliding displacement and hold the lens in place has been for an assistant to constantly monitor the lens position and using a rod or other extension to push the lens back to a desired location. Such assistant need be experienced in vitreoretinal surgery in order to perform this task.

One method that has been developed for overcoming the problem of lens movement is disclosed in U.S. Pat. No. 5,963,301. in that patent, the lens is constructed with a flange that is shaped to conform to the general curvature of an average eye. Accordingly, the flange generally will not seat in a sealing arrangement on the surface of the eye without being pressed down. The flange is large enough to extend over the sclera of the eye and has a fixed radius of curvature that is substantially flatter than the curvature of contact surface of the lens so that the lens device tends to be stabilized and centered over the cornea of the eye. The flange is formed with a number of peripheral opening or recesses that are sized to accommodate various types of instruments that may need to be inserted into the eye during surgery. The flange may also be formed with fittings to which a vacuum may be applied in order to pull the flange into contact with the eye by creating a vacuum between the flange and eye to better hold the lens device in position.

Another method that has been developed for overcoming the problem of contact lens movement during surgery is disclosed in U.S. Pat. No. 6,120,147. In this patent, the authors recognize that there are issues with the typical glass or inflexible contact lens and therefore propose to replace that lens with a flexible lens having a relatively flexible flange that can that can flex relative to the contact lens without deforming the flexible lens. The flange in this instance is formed with a curvature that is less than the radius of curvature of the average sclera so that it can be secured to a range of different size eyes. In use, this lens device is pressed down into full contact with the eye so that the lens becomes fixed in place by capillary action. In order for this to be successful, it is necessary for the lens and flange to be kept to a very light weight.

SUMMARY OF THE INVENTION

Applicant has found that the concept embodied in the prior art is based on a false premise. In each of the prior art devices it is assumed that some form of vacuum or capillary suction is necessary to hold the lens in position. Applicant has discovered that this effect can be achieved without relying on vacuum attachment by simply creating a weight to hold the lens in position. In a preferred form, such weight can be developed by using a moisture absorbent material placed about the periphery of the lens and soaking the material with a sterile fluid, such as the fluid that is used during surgery to wash the eye. The material can be of various shapes so long as there is provided a central aperture for the lens. In one form, the lens and material combination can be prepared prior to surgery with the material being adhered to the edge of the lens.

BRIEF DESCRIPTION OF THE DRAWINGS

For a better understanding of the present invention, reference may be made to the Detailed Description taken in conjunction with the attached drawings in which.

DETAILED DESCRIPTION

Figure 1:
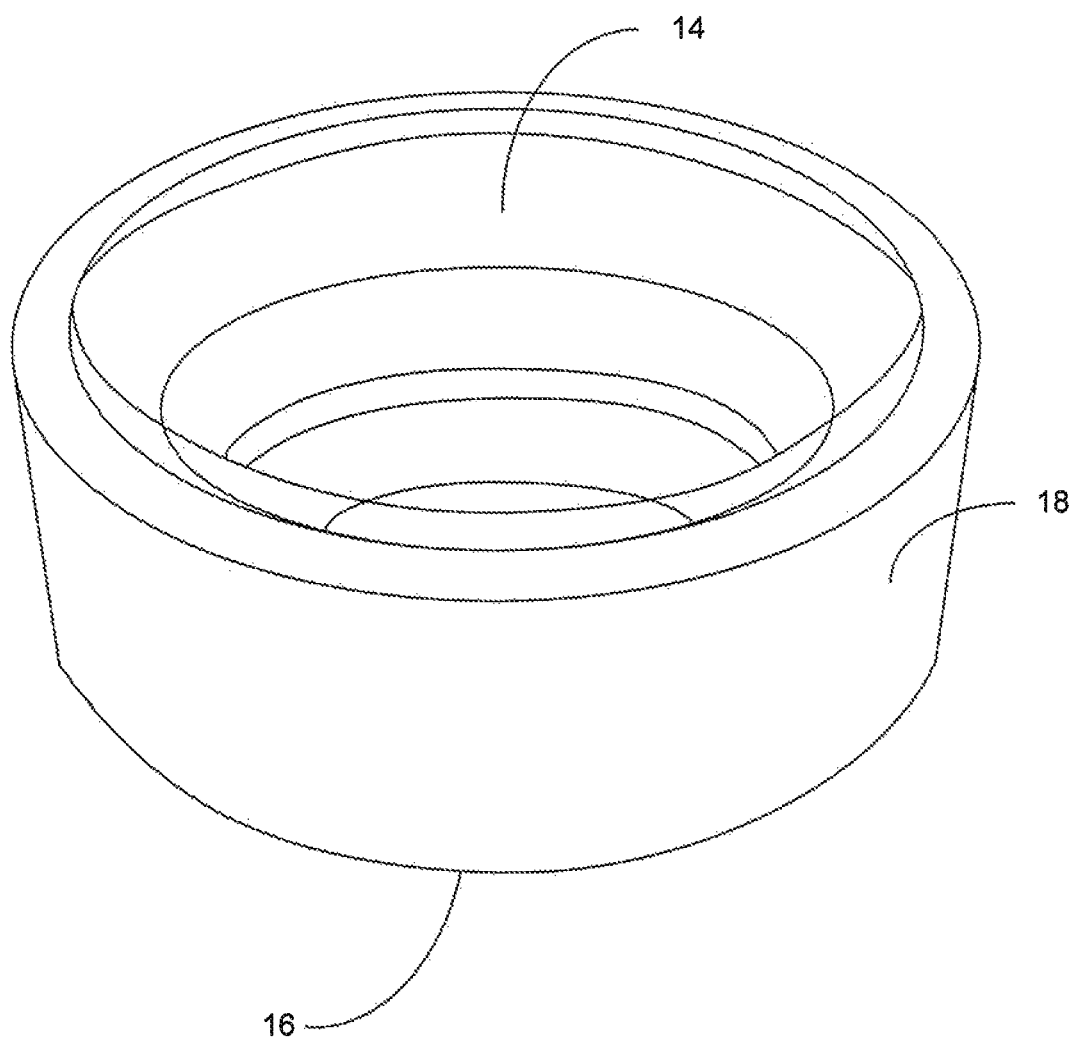
FIG. 1 is a perspective view of one form of contact lens with which the present invention may be used.

FIG. 1 is a perspective view of one form of contact lens 10 used in vitreoretinal surgery. The lens 10 has curved shaped surfaces on both faces 14, 16 with at least one face being shaped to fit an average curvature of the cornea of a human eye. The lens 10 has a vertical sidewall 18 having a height in the range of about 3.5 mm. The diameter of the lens is in the range of about 12 mm. This form of lens 10 is used when it is desired to provide a wide field of view in the posterior of the eye such as is needed for viewing the posterior fundus and central vitreous. Other shapes of the lens could be used for different viewing requirements although the surface that is in contact with the eye is dictated by the general shape of the eye.

Figure 2:
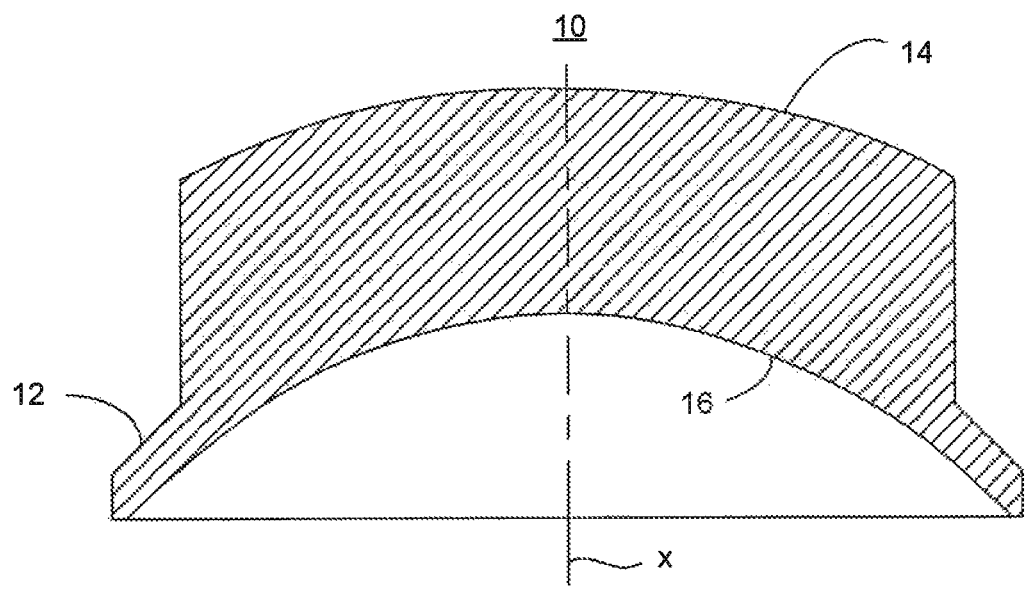
FIG. 2 is a cross-sectional view of the lens of FIG. 1.

A cross-sectional view of a slightly different form of the lens 10 is shown in FIG. 2. The only difference is in the addition of a circumscribing flange 12 which is curved to fit the average curvature of an eye. This view better illustrate the upper concave surface 14 and the lower concave surface 16. The centerline is indicated at "x" about which the lens is symmetrical.

Figure 3:
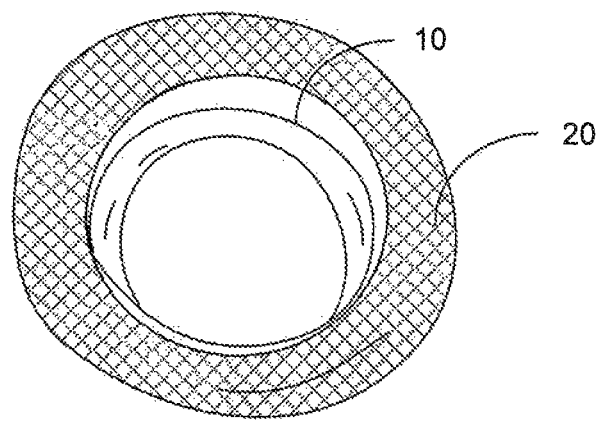
FIG. 3 is a perspective view of the lens of FIG. 1 with the present invention coupled thereto.

FIG. 3 is a perspective view of the lens 10 of FIG. 1 with the inventive flange 20 positioned about the lens. The flange 20 is preferably formed of a soft, sponge-like material that is highly absorbent. One such material is marketed by DeRoyal Medical Products, a division of DeRoyal Industries, Inc., under their product No. 25-201 as an instrument wipe made from polyvinyl alcohol. The flange 20 may be cut to shape to fit about the lens 10 with a central aperture that is slightly smaller than the lens to create a stretch fit with the lens. In this embodiment, the central aperture may be scissor cut to form the aperture smaller than the lens diameter so that the edges of the flange around the aperture rest on the outer periphery of the contact lens. The flange extends radially outward about 3 mm.

Figure 4A:
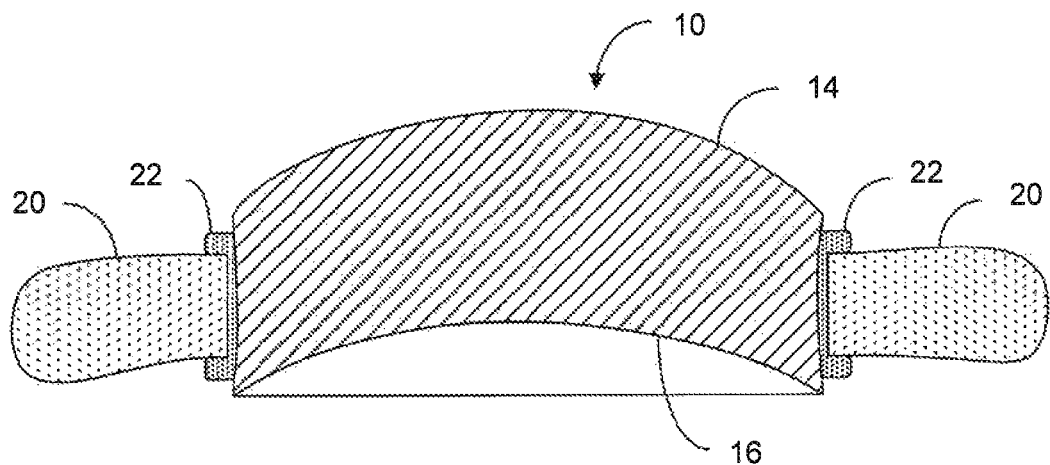
FIGS. 4a, 4b and 4c are cross-sectional views of the assembly of FIG. 3 illustrating different methods and apparatus for coupling the present invention to a contact lens.
Figure 4B:
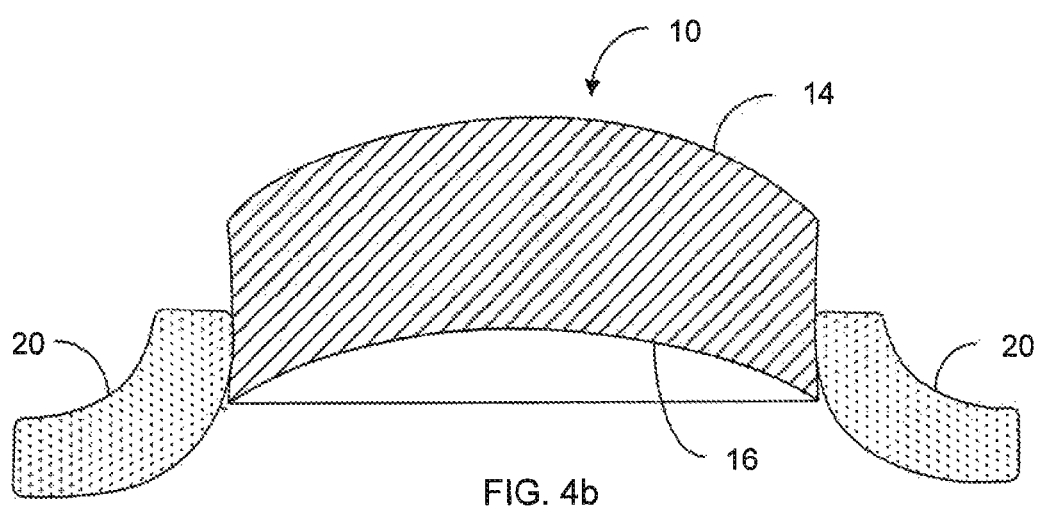
Figure 4C:
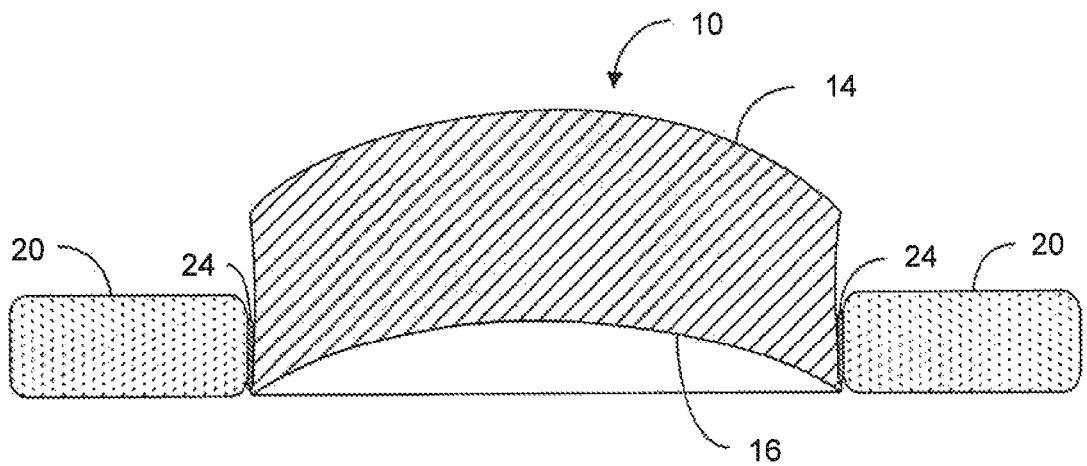

FIG. 4 is a cross-sectional view illustrating the lens 10 of FIG. 2 with the flange 20 attached by means of a separate attachment ring 22. The material of the flange 20 may be adhesively bonded to the attachment ring 22. The ring 22 may be formed of an elastic material of various types that are capable of being sterilized, such as, for example, a vinyl material.

Figure 5:
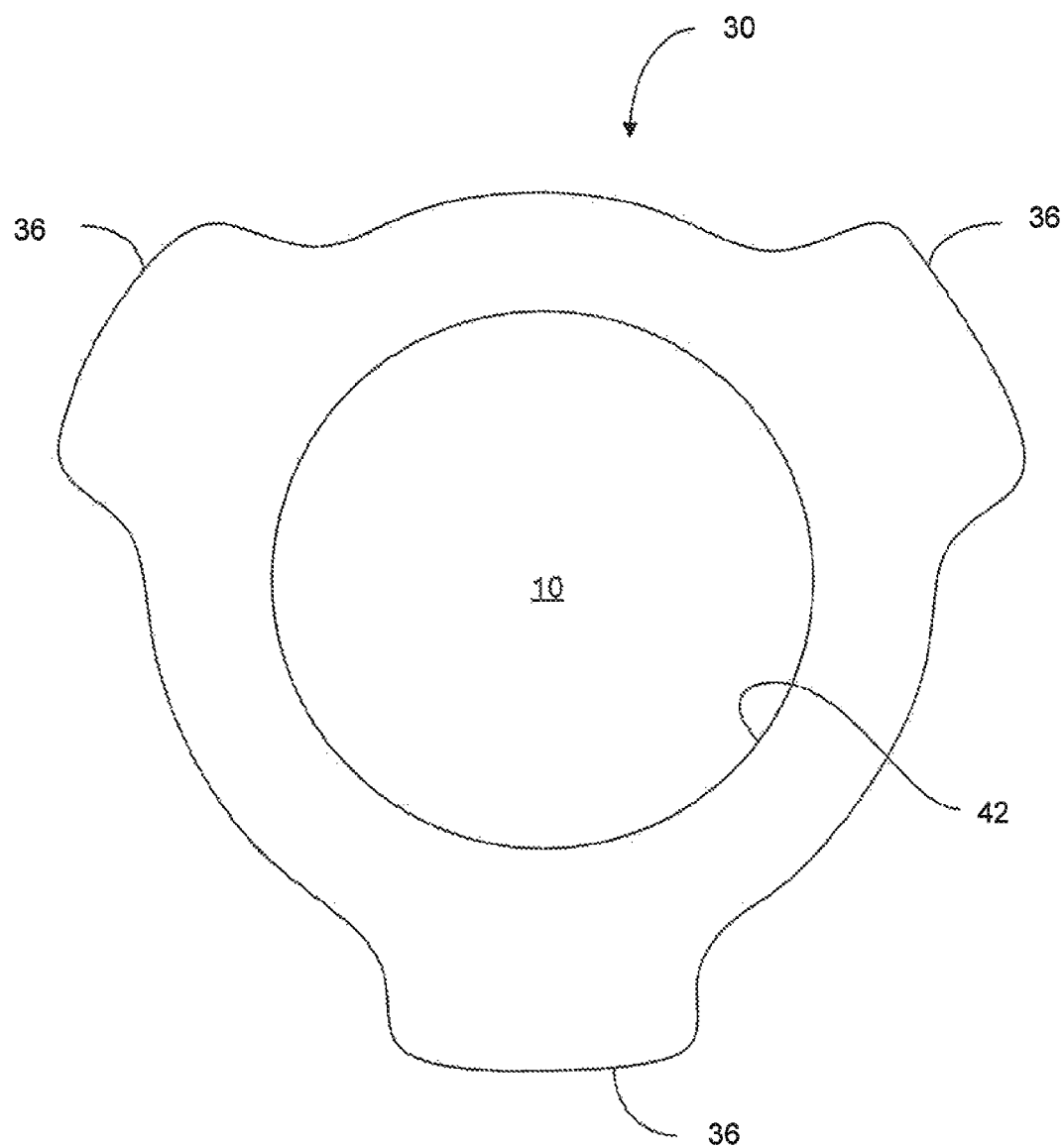
FIGS. 5, 6 and 7 are top plan views showing different configurations for the present invention
Figure 6:
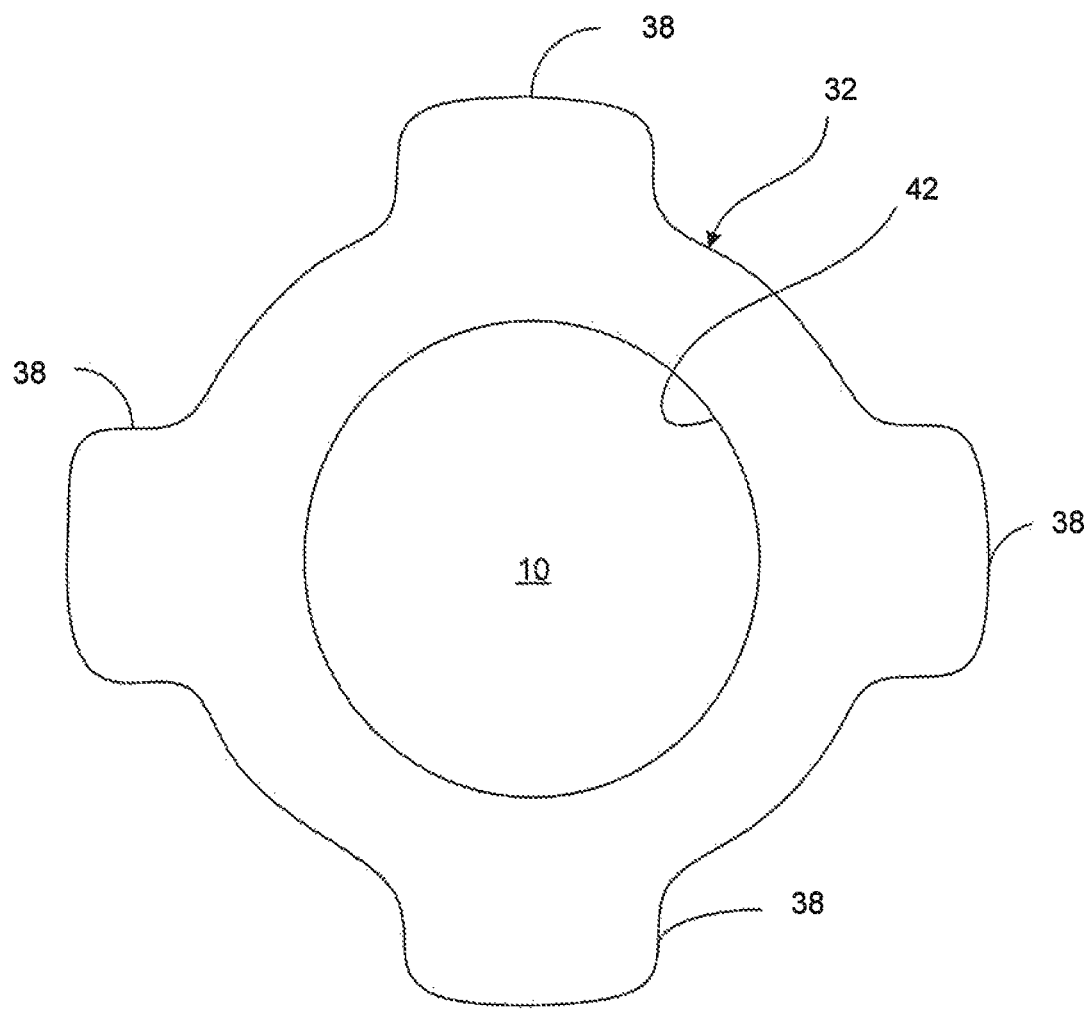
Figure 7:
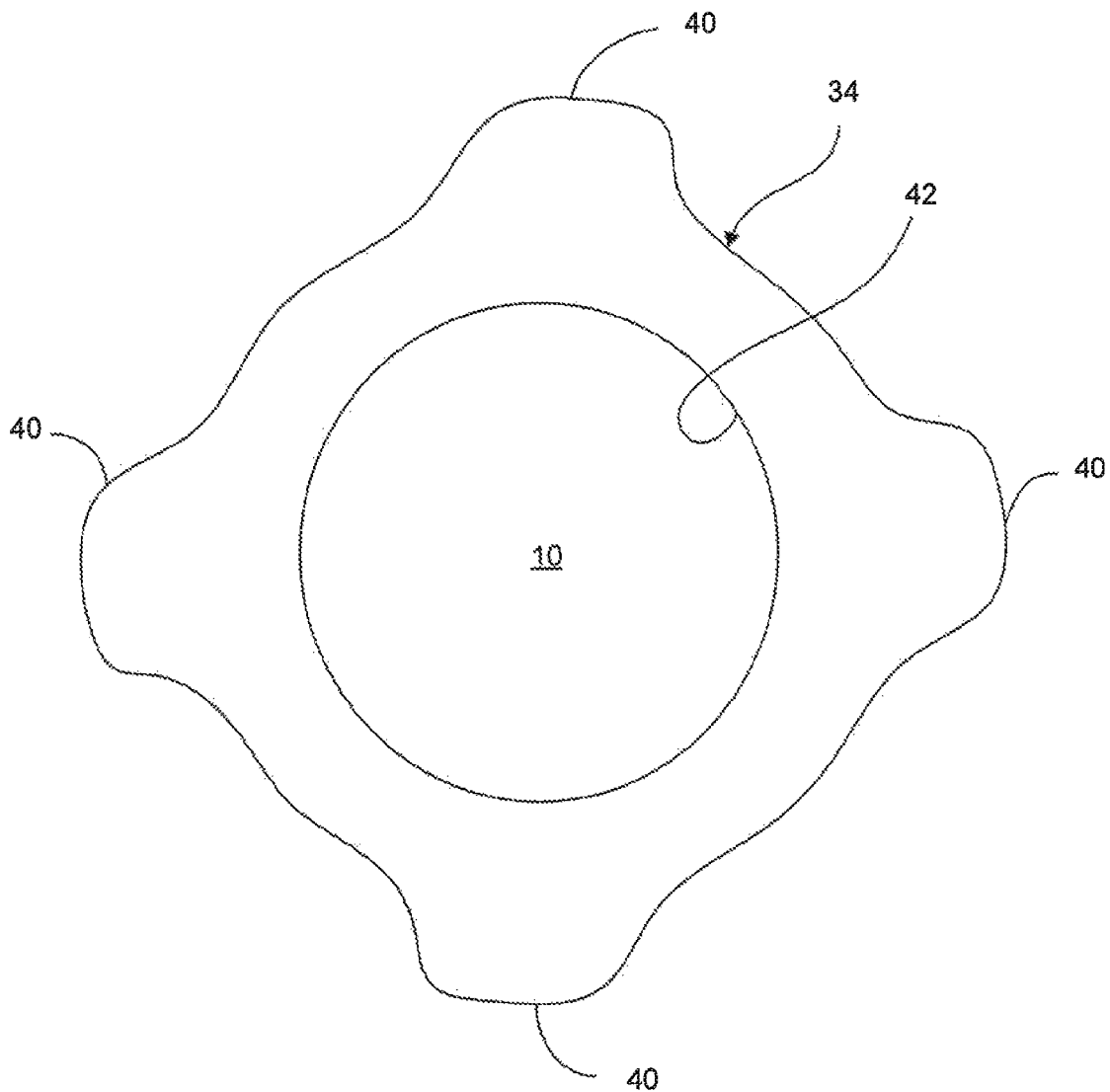

FIGS. 5, 6 and 7 show alternate forms of the outer flange 20, identified as flange 30, 32 and 34 in the respective figures, in which the flange has been created with a defined shape. In these embodiments, the flange may be formed by a stamping operation using a cutting die to cut the flange from a sheet of the absorbent material. In FIG. 5, the flange 30 has three extending legs 36 that create a large surface area to increase the weight of the flange when wetted so as to assist in holding the lens 10 in position on an eyeball. FIGS. 6 and 7 differ from FIG. 5 in having four legs 38 and 40, respectively. In FIG. 6, the legs 38 are symmetrically positioned about the flange 32 while in FIG. 7, the legs 40 are asymmetric about the flange 34. In each design of FIGS. 5, 6 and 7, the flanges 30, 32 and 34 may be joined to the lens 10 using an intermediate attachment ring such as that shown at 22 in FIG. 4. Alternately, the central opening 42 in each flange 30, 32 and 34 may be sized such that the wetted material of the flange can be stretched about the lens 10 and held in place by friction between the material and lens.

In use, the lens 10 is mated with the flange 20 and the combination is then placed on the wetted eye of a patient. Additional wetting compound, such as a sterile saline solution, is then dripped or sprayed onto the flange 20 until the flange is generally saturated. The lens can then be moved as necessary for viewing and the wetted flange will hold the lens into the desired position.

Applicant believes that the mere weight of the wetted flange 20 creates sufficient force to hold the lens 10 in a fixed position. However, it is also recognized that the material of the flange, due to its soft and flexible texture and its intimate contact with the eye surface, may create some degree of adhesion, perhaps just from friction between the flange material and the eye surface.

It will be apparent that various modifications and adaptations may be made to the lens and flange arrangements described above without departing from the spirit and scope of the invention. It is intended therefore that the appended claims be construed to cover all such modifications and adaptations as fall within the true spirit of the invention.

What is claimed is:

1. A contact lens assembly having a central lens and a circumscribing flange, the lens having an eye contact surface shaped generally to a radius of curvature of a cornea of an eye, the flange comprising a sterile sponge liquid absorbent flexible material having a central aperture for fitting snugly about an outer circumference of the lens and extending radially outward therefrom such that the flange conforms to the shape of the eye to hold the lens in a desired position upon the flexible material of the flange being saturated in a sterile solution.

2. The contact lens assembly of claim 1 and including an attachment ring separate from the lens and the flange, where the attachment ring is fixed about the central aperture of the flexible material, the attachment ring fitting about the lens for holding the flexible material to the lens.

3. The contact lens assembly of claim 1 wherein the flexible material is held to the lens by friction fit.

4. The contact lens assembly of claim 1 wherein the flexible material is adhesively bonded to the lens.

5. The contact lens assembly of claim 1 wherein the flexible material comprises a polyvinyl alcohol material.

6. The contact lens assembly of claim 1, wherein the central lens has an upper concave surface and a lower concave surface, wherein the upper and lower concave surfaces are shaped to fit an average curvature of the cornea.

7. The contact lens assembly of claim 1, wherein a diameter of the central aperture is smaller than a diameter of the outer circumference to provide a stretch fit between the flange and the lens.

8. A method for stabilizing a lens on a patient's eye during vitreoretinal surgery, the lens including a contact lens element having a posterior surface with a shape substantially corresponding to a shape of an average cornea for transmitting light emanating from the patient's eye for viewing a structure of the patient's eye, the method comprising:
    surrounding the contact lens element with a liquid absorbable flange formed of a sterile sponge liquid absorbent flexible material;
    saturating the flange with sterile liquid such that the flange conforms to the shape of any eye due to a weight of the liquid absorbed by the material; and
    holding the lens in a fixed position with the saturated flange based on the weight of the liquid absorbed by the material.

9. The method of claim 8 wherein the flange is attached to the contact lens by an attachment ring integral with the flange.

10. The method of claim 9 wherein the attachment ring is adhesively bonded to the contact lens.

11. The method of claim 9 wherein the attachment ring is removable from the contact lens.

12. The method of claim 8 wherein the flange is discontinuous about the periphery of the contact lens.

13. The method of claim 8 wherein the flange is attached to the contact lens by an attachment ring separate from the lens and the flange.

14. An improvement for a contact lens assembly having a central lens and a circumscribing flange, the lens having an eye contact surface shaped generally to a radius of curvature of a cornea of an eye, wherein vacuum suction or capillary traction is used to hold the lens in position on the eye, the improvement comprising:
    a weight of sterile solution absorbed by the circumscribing flange to hold the lens in position on the eye without vacuum suction or capillary traction.

* * * * *